United States Patent
Nuopponen et al.

(10) Patent No.: US 10,119,919 B2
(45) Date of Patent: Nov. 6, 2018

(54) METHOD AND DEVICE FOR MONITORING THE QUALITY OF NANOFIBRILLAR CELLULOSE

(71) Applicant: UPM-KYMMENE CORPORATION, Helsinki (FI)

(72) Inventors: Markus Nuopponen, Helsinki (FI); Juha Tamper, Levanen (FI); Isko Kajanto, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 15/321,204

(22) PCT Filed: Apr. 27, 2015

(86) PCT No.: PCT/FI2015/050285
§ 371 (c)(1),
(2) Date: Dec. 22, 2016

(87) PCT Pub. No.: WO2016/001480
PCT Pub. Date: Jan. 7, 2016

(65) Prior Publication Data
US 2017/0160206 A1    Jun. 8, 2017

(30) Foreign Application Priority Data
Jun. 30, 2014 (FI) .................... 20145631

(51) Int. Cl.
*G01N 21/00* (2006.01)
*G01N 21/82* (2006.01)
(Continued)

(52) U.S. Cl.
CPC ............ *G01N 21/82* (2013.01); *C08L 1/00* (2013.01); *C08L 1/02* (2013.01); *C08L 1/04* (2013.01);
(Continued)

(58) Field of Classification Search
CPC ........ D21C 9/002; D21C 9/004; D21C 9/005; D21C 9/007; D21H 11/18; D21H 11/10; G01N 21/82; C08L 1/00; G05D 21/00
(Continued)

(56) References Cited

U.S. PATENT DOCUMENTS

| 4,801,204 A | 1/1989 | Nakamura et al. |
| 5,786,894 A * | 7/1998 | Shields .................... G01N 1/38 250/574 |

(Continued)

FOREIGN PATENT DOCUMENTS

| WO | 2011064441 A1 | 6/2011 |
| WO | 2012168562 A1 | 12/2012 |

(Continued)

OTHER PUBLICATIONS

International Preliminary Report on Patentability dated Jun. 17, 2016; International Application No. PCT/FI2015/050285; International Filing Date Apr. 27, 2015 (6 pages).
(Continued)

Primary Examiner — Hoa Pham
(74) Attorney, Agent, or Firm — Cantor Colburn LLP (57) ABSTRACT

One embodiment provides a method for monitoring the quality of nanofibrillar cellulose produced in a process comprising disintegrating fibers of cellulose pulp, the method comprising measuring in real-time optically the turbidity of a dispersion containing nanofibrillar cellulose obtained from a disintegrating process, and determining the quality of said produced nanofibrillar cellulose using a correlation between the measured turbidity and said quality of the produced nanofibrillar cellulose, wherein lowered turbidity indicates increased quality of the nanofibrillar cellulose. One embodiment provides a device for monitoring the quality of nanofibrillar cellulose produced in a process
(Continued)

comprising disintegrating fibers of cellulose pulp, arranged to carry out said method.

40 Claims, 8 Drawing Sheets

(51) Int. Cl.
*D21H 11/18* (2006.01)
*C08L 1/02* (2006.01)
*C08L 1/04* (2006.01)
*C08L 1/00* (2006.01)
*D21C 3/00* (2006.01)
*G05D 21/00* (2006.01)

(52) U.S. Cl.
CPC ............... *D21C 3/00* (2013.01); *D21H 11/18* (2013.01); *G05D 21/00* (2013.01)

(58) Field of Classification Search
USPC ...... 356/73, 335–343, 432–440; 106/163.01; 162/181.2, 26, 261, 60
See application file for complete search history.

(56) References Cited

U.S. PATENT DOCUMENTS

| | | | |
|---|---|---|---|
| 6,202,946 B1 | 3/2001 | Virtanen | |
| 6,311,550 B1* | 11/2001 | Lehmikangas | .... G01N 15/0227 356/338 |
| 8,120,769 B2* | 2/2012 | Rust | ..................... G01B 11/024 356/238.1 |
| 8,911,591 B2* | 12/2014 | Ankerfors | .............. D21C 9/002 162/62 |
| 2005/0231716 A1* | 10/2005 | Ryu | ....................... G01N 21/51 356/318 |
| 2005/0272836 A1* | 12/2005 | Yaginuma | ................. A23F 3/40 524/27 |
| 2009/0185162 A1* | 7/2009 | Shakespeare | ............. G01J 3/10 356/51 |
| 2009/0255876 A1 | 10/2009 | Dunbar | |
| 2010/0282654 A1* | 11/2010 | Hauschild | ............. C02F 3/1268 210/151 |
| 2013/0255096 A1* | 10/2013 | Kampris | ................. D21F 5/187 34/85 |
| 2014/0374045 A1* | 12/2014 | Nuopponen | ........... D21C 9/007 162/181.2 |
| 2015/0034263 A1* | 2/2015 | Nuopponen | ............... C08L 1/04 162/57 |
| 2016/0289894 A1* | 10/2016 | Kajanto | ................. D21C 5/005 |

FOREIGN PATENT DOCUMENTS

| | | |
|---|---|---|
| WO | 2013117823 A1 | 8/2013 |
| WO | 2013121108 A1 | 8/2013 |
| WO | 2014184438 A1 | 11/2014 |

OTHER PUBLICATIONS

International Search Report dated Jun. 22, 2015; International Application No. PCT/FI2015/050285; International Filing Date Apr. 27, 2015 (3 pages).

Written Opinion dated Jun. 22, 2015; International Application No. PCT/FI2015/050285; International Filing Date Apr. 27, 2015 (5 pages).

* cited by examiner

METHOD AND DEVICE FOR MONITORING THE QUALITY OF NANOFIBRILLAR CELLULOSE

CROSS-REFERENCE TO RELATED APPLICATIONS

This application is a National Stage application of PCT/FI2015/050285, filed Apr. 27, 2015, which claims the benefit of Finnish Application No. 20145631, filed Jun. 30, 2014, both of which are incorporated by reference herein in their entirety.

FIELD OF THE APPLICATION

Background

Lignocellulose-containing fibers can be disintegrated into smaller parts by detaching fibrils which act as components in the fiber walls, wherein the particles obtained become significantly smaller in size. The properties of so-called nanofibrillar cellulose thus obtained differ significantly from the properties of normal pulp. It is possible to use nanofibrillar cellulose as an additive in papermaking and to increase the internal bond strength (interlaminar strength) and tensile strength of the paper product, as well as to increase the tightness of the paper. Nanofibrillar cellulose also differs from pulp in its appearance, because it is a gel-like material in which the fibrils are present in water dispersion. Because of the properties of nanofibrillar cellulose, it has become a desired raw material, and products containing it would have several uses in industry, for example as an additive in various compositions.

Currently there is no existing technology to measure the development of nanocellulose during the production process. Generally, the quality control measurements have been made from diluted samples in a laboratory after the production. This is however slow and laborious and no information can be obtained during the process so it is not possible to control the process as a feedback to the measured properties of the product.

SUMMARY

In a fibrillation process of cellulose it was found out that real-time turbidity measurements correspond to laboratory measurements of the quality of the produced nanofibrillar cellulose dispersion at low consistency. The correlation of the turbidity and the quality of the nanofibrillar cellulose can be utilized to determine the quality of the product instantly from the process flow.

One embodiment provides a method for monitoring the quality of nanofibrillar cellulose produced in a process comprising disintegrating fibers of cellulose pulp, the method comprising measuring in real-time optically the turbidity of a dispersion containing nanofibrillar cellulose obtained from said disintegrating process, and determining the quality of said produced nanofibrillar cellulose using a correlation between the measured turbidity and said quality of the produced nanofibrillar cellulose, wherein lowered turbidity indicates increased quality of the nanofibrillar cellulose.

One embodiment provides a device for monitoring the quality of nanofibrillar cellulose produced in a process comprising disintegrating fibers of cellulose pulp, the device being arranged to monitor a dispersion containing said produced nanofibrillar cellulose obtained from a disintegrating device, the monitoring device comprising means for measuring optically the turbidity of said dispersion in real-time, and means for determining the quality of said produced nanofibrillar cellulose using a correlation between the measured turbidity and said quality of the produced nanofibrillar cellulose, wherein lowered turbidity indicates increased quality of the nanofibrillar cellulose.

The feature that the measurements are carried optically enables the measurements being carried out in real-time. Further, the device arranged to carry out the method may be arranged to a variety of disintegrating devices.

The feature that the measurement is carried out real-time provides a simple procedure for monitoring the quality. No separate time-consuming steps, such as sampling, treatment of the samples, transport to a laboratory and/or further laboratory tests are required. As there is no delay in obtaining the results, i.e. the results are obtained practically in real-time, an effect of saving time and money is achieved. The real-time results further provide an effect of enabling the controlling the process in real-time as a feedback for the measurements.

The optical measurements used in the embodiments enable efficient measurements at substantially high consistency. Further, a change in the consistency during the process does not interfere with the turbidity measurement. This provides an effect that the measurement can be carried from an untreated product flow obtained directly from the process. The sample does not have to be diluted or otherwise treated in order to be analyzed.

DETAILED DESCRIPTION

As used herein, the term "nanofibrillar cellulose" refers to cellulose microfibrils or microfibril bundles separated from cellulose-based fiber raw material. These fibrils are characterized by a high aspect ratio (length/diameter): their length may exceed 1 μm, whereas the diameter typically remains smaller than 200 nm. The smallest fibrils are in the scale of so-called elementary fibrils, the diameter being typically in the range of 2-12 nm. The dimensions and size distribution of the fibrils depend on the refining method and efficiency. Nanofibrillar cellulose may be characterized as a cellulose-based material, in which the median length of particles (fibrils or fibril bundles) is not greater than 50 μm, for example in the range of 1-50 μm, and the particle diameter is smaller than 1 μm, suitably in the range of 2-500 nm. In case of native fibril cellulose, in one embodiment the average diameter of a fibril is in the range of 5-100 nm, for example in the range of 10-50 nm. Nanofibrillar cellulose is characterized by a large specific surface area and a strong ability to form hydrogen bonds. In water dispersion, the nanofibrillar cellulose described herein typically appears as either light or turbid gel-like material. Depending on the fiber raw material, nanofibrillar cellulose may also contain small amounts of other wood components, such as hemicellulose or lignin. The amount is dependent on the plant source. Often used parallel names for nanofibrillar cellulose include nanofibrillated cellulose (NFC), which is often simply called nanocellulose, and microfibrillated cellulose (MFC).

Different grades of nanofibrillated cellulose may be categorized based on three main properties: (i) size distribution, length and diameter (ii) chemical composition, and (iii) rheological properties. Any of these methods alone is not suitable to describe a grade, i.e. the methods should be used in parallel. Examples of different grades include native (or non-modified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low, low viscosity vs. high viscosity etc. The fibrillation technique and the chemical pre-modification have an influence on the fibril size distribution. Typically, non-ionic grades have wider fibril diameter (for example in the range of 10-100 nm, or 10-50 nm) while the chemically modified grades are a lot thinner (for example in the range of 3-20 nm). Distribution is also narrower for the modified grades. Certain modifications, especially TEMPO-oxidation, yield shorter fibrils.

Depending on the raw material source, e.g. hardwood (HW) vs. softwood (SW) pulp, different polysaccharide composition exists in the final fibril cellulose product. Commonly, the non-ionic grades are prepared from bleached birch pulp, which yields high xylene content (25% by weight). Modified grades are prepared either from HW or SW pulps. In those modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

In an aqueous environment, a dispersion of cellulose nanofibers forms a viscoelastic hydrogel network. The gel is formed at relatively low concentrations of for example 0.1-0.2% by dispersed and hydrated entangled fibrils. The viscoelasticity of the NFC hydrogel may be characterized for example with dynamic oscillatory rheological measurements.

As regards rheology, the nanofibrillar cellulose hydrogels are shear-thinning materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent on the raw material and the disintegration method. Mechanical disintegration of the cellulose raw material may be carried out with any suitable equipment such as a refiner, grinder, homogenizer, colloider, friction grinder, pin mill, ultrasound sonicator, fluidizer such as microfluidizer, macrofluidizer or fluidizer-type homogenizer. The disintegration treatment is performed at conditions wherein water is sufficiently present to prevent the formation of bonds between the fibers.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The energy taken by the refining work is normally expressed in terms of energy per processed raw material quantity, in units of e.g. kWh/kg, MWh/ton, or units proportional to these. The expressions "disintegration" or "disintegration treatment" may be used interchangeably with "fibrillation".

The fiber material dispersion that is subjected to fibrillation is a mixture of fiber material and water, also herein called as "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

Dispersion is a system in which material comprises more than one phase where at least one of the phases consists of finely divided phase domains, often in the colloidal size range, dispersed throughout a continuous phase (IUPAC definition). The continuous phase of the dispersion is a dispersion medium, for example water. In general a dispersion of solid particles in a liquid is called a suspension. Especially in some cases a coarse dispersion is called a suspension.

The fiber material that is used as the starting material may be based on any plant material that contains cellulose. The plant material may be wood. The wood may be from softwood trees such as spruce, pine, fir, larch, douglas fir or hemlock, or from hardwood trees such as birch, aspen, poplar, alder, eucalyptus or acasia, or from a mixture of softwood and hardwood. Nonwood material may be from for example agricultural residues, grasses or other plant substances, such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed.

Turbidity is the cloudiness or haziness of a fluid caused by individual particles (total suspended or dissolved solids) that are generally invisible to the naked eye. There are several practical ways measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

One embodiment provides a method for monitoring the quality of nanofibrillar cellulose produced in a process comprising disintegrating fibers of cellulose pulp, generally by one or more pulp disintegrating devices, the method comprising measuring in real-time optically the turbidity of a dispersion containing nanofibrillar cellulose obtained from said disintegrating process, generally from one or more pulp disintegrating device(s), and defining or determining the quality of said produced nanofibrillar cellulose using a correlation between the measured turbidity and said quality of the produced nanofibrillar cellulose, wherein lowered turbidity indicates increased quality of the nanofibrillar cellulose. As a result a value representing the quality of the nanofibrillar cellulose is obtained or outputted. Preferably the process is a continuous process, but the method may be also applied to batch processes.

The process comprising disintegrating the fibers of cellulose pulp may be carried out by using any suitable fibrillating method and/or device, for example by using a disperser or a homogenizer, to obtain nanofibrillated cellulose. Other examples of such devices include refiner, grinder, colloider, friction grinder, ultrasound sonicator, and fluidizer such as microfluidizer, macrofluidizer or fluidizer-type homogenizer.

The expression "real-time" as used herein refers to monitoring which is carried out during the disintegrating process, i.e. the product directly obtained from the disintegration process is monitored and analyzed without any further steps such as taking, preparing or transporting samples. In practice the monitoring is carried out from a flow of the product suspension or dispersion and continuous results are obtained. The real-time measurement may be carried out for example in-line or on-line. In the in-line measurement the measurement is carried out from the process flow, for example a process tube or pipeline, i.e. the sensors or instruments are situated in a flow-through system. In-line measurement is closely related to in situ measurement. In the on-line measurement the measurement is carried out from a side flow, for example a tube or pipeline branching from the main flow. In many cases the in-line measurement is preferred, especially when the instrument needs to be installed in a tube having a large diameter.

The optical measurements may be based on different optical properties of the material. For example the light scattered from the particles in the dispersion may be measured. Also the polarization of the scattered light may be measured, or the change in the polarization of the scattered light. The light absorbed in the dispersion may be measured. In general such optical measurements may measure the turbidity of the dispersion, but it was found out that they correlate well also with the overall quality of the fibrillated cellulose, especially with ionic grades. The turbidity may also correlate with the viscosity of the product. In the particle size reduction when producing nanocellulose, the fibers are transformed into thin fibrils with high aspect ratio, and the viscosity of the suspension is therefore also high. As the surface area of the fibers increases, also the viscosity increases. Simultaneously, because in the size reduction the particles become narrower, their effectiveness in interacting with light decreases. Therefore, most often a simultaneous increase of viscosity and decrease of turbidity can be seen.

In one embodiment the turbidity measurement is a light scattering measurement. The propensity of particles to scatter a light beam focused on them is considered a meaningful measure of turbidity in water. Turbidity measured this way may be carried out using a nephelometer with the detector set up to the side of the light beam. More light reaches the detector if there are lots of small particles scattering the source beam than if there are few. The units of turbidity from a calibrated nephelometer are called Nephelometric Turbidity Units (NTU). To some extent, how much light reflects for a given amount of particulates is dependent upon properties of the particles like their shape, color, and reflectivity. For this reason (and the reason that heavier particles settle quickly and do not contribute to a turbidity reading), a correlation between turbidity and total suspended solids (TSS) is somewhat unique for each location or situation.

A nephelometer measures suspended particulates by employing a light beam (source beam) and a light detector set to one side (often 90°) of the source beam. Particle density is then a function of the light reflected into the detector from the particles. To some extent, how much light reflects for a given density of particles is dependent upon properties of the particles such as their shape, color, and reflectivity. Nephelometers are calibrated to a known particulate, and they may use environmental factors (k-factors) to compensate lighter or darker colored dusts accordingly. A nephelometric turbidimeter always monitors light reflected off the particles and not attenuation due to cloudiness.

In one embodiment the turbidity measurement is an absorption measurement. In an absorption system, a beam of light is interrupted by a sample of liquid. Light enters the liquid and the amount of light leaving the liquid is reduced due to scattering and absorption when the light enters the liquid container (e.g. the window glass of the meter), reflection from the glass window/liquid interface, absorption due to the color of the liquid, scattering and absorption of light due to suspended particles and then the same sequence of scattering and absorption at the liquid/window interface and window/air interfaces of the receiving light scanner. The losses due to all liquid scattering and all absorption of the particles constitute turbidity. This may be also called as "lost light", "straight through," or "transmission turbidimeter".

In one embodiment the turbidity measurement is a measurement of a change in the polarization of scattered light. This technique is based on double refraction of fibers, wherein the cellulose fibers rotate the plane of light polarization. The measurement is independent of pulp color and brightness variations as well as ash fluctuations. One example of such device using light polarization is Metso LC.

The basic turbidimeter instrument contains a light source, optionally a sample container or a cell, and one or more photodetector(s) (or light detector(s)) to sense the scattered light. The most common light source used is a tungsten filament lamp. The spectral output (band of wavelength light produced) of these lamps is generally characterized by "color temperature," which is the temperature in which a black body radiator must be operated to produce a certain color. The tungsten filament lamps are incandescent lamps and are termed "polychromatic," since they have a fairly wide spectral band that includes many different wavelengths of light, or colors. The presence of the various wavelengths can cause interference in the turbidity measurements as natural color and natural organic matter in the sample can absorb some specific wavelengths of light and reduce the intensity of the scattered light.

Some turbidimeter designs utilize monochromatic light sources, such as light emitting diodes (LEDs), lasers, mercury lamps, and various lamp filter combinations. Monochromatic light has a very narrow band of light wavelengths (only a few colors). By selecting light wavelengths that are not normally absorbed by organic matter, the monochromatic light source can be less susceptible to interference by sample color.

In one embodiment the optical measurement is carried out at a wavelength in the range of 260-900 nm, such as wavelength in the range of 400-890 nm. A shorter wavelength will scatter more therefore detecting smaller particles, and being more sensitive at low consistency.

In turbidimeters, photodetectors detect the light produced from the interaction of the incident light and the sample volume and produce an electronic signal that is then converted to a turbidity value. These detectors can be located in a variety of configurations depending on the design of the instrument. The four types of detectors commonly used include photomultiplier tubes, vacuum photodiodes, silicon photodiodes, and cadmium sulfide photoconductors.

The on-line instruments typically utilize a single beam or modulated four beam design. On-line ratio turbidimeters are also available. On-line instruments typically sample a side stream split off from the treatment process. The sample flows through the on-line instrument for measurement and then is wasted to a drain or recycled through the treatment process. Supervisory Control and Data Acquisition (SCADA) instrumentation and remote telemetry can also be connected to on-line instruments to collect data for analysis or to control the disintegrating process and devices therein based on the turbidities measured.

In one embodiment the turbidity measurement is carried out at a consistency of said dispersion in the range of 0.15-10%. In one embodiment the turbidity measurement is carried out at a consistency of said dispersion in the range of 0.5-8%. In one embodiment the turbidity measurement is carried out at a consistency of said dispersion in the range of 1-5%, for example in the range of 1.5-4%, or in the range of 2-3%. In one example the consistency is about 2.4%, as used for example in the tests. No dilution of the dispersion or the sample is required before the measurement. The resolution of the measurement is better at such substantially high consistencies. However, in practice, at a consistency of 5% and above, the dispersion begins to have properties of solid matter. At higher consistencies, such as about 2.5% and above a fibril network begins to form, whereas at a very low consistency of about 0.1% the particles are completely separate.

The measurement is carried out generally at the process temperature and/or pressure, for example at a temperature in the range of about 10-80° C. and/or at a pressure of about 1-6 bar, for example about 1-2 bar. In one example heat is used to promote the fibrillation at a temperature in the range of 40–80° C.

In general, it is desired to keep the consistency constant. Unlike in certain other measurements, a change in the consistency is not measured, but the change in the quality of the product. Even though the consistency affects the light permeability in the dispersion, the change in the consistency does not usually interfere the measurement significantly as the measurement of the turbidity is more sensitive.

Generally, during the fibrillation of the cellulose the change in the size, such as the diameter of the fibrils, towards a nanoscale product makes the suspended fibril cellulose more transparent. As the transparency increases the turbidity decreases as the particle size diminishes during the fibrillation process. Finally, at least in theory, a completely transparent dispersion of nanofibrillar cellulose is obtained. This is considered representing a product with high quality. In practice, it is the amount of non-fibrillated fibers still left in the dispersion which is measured in the present method.

Figure 13:
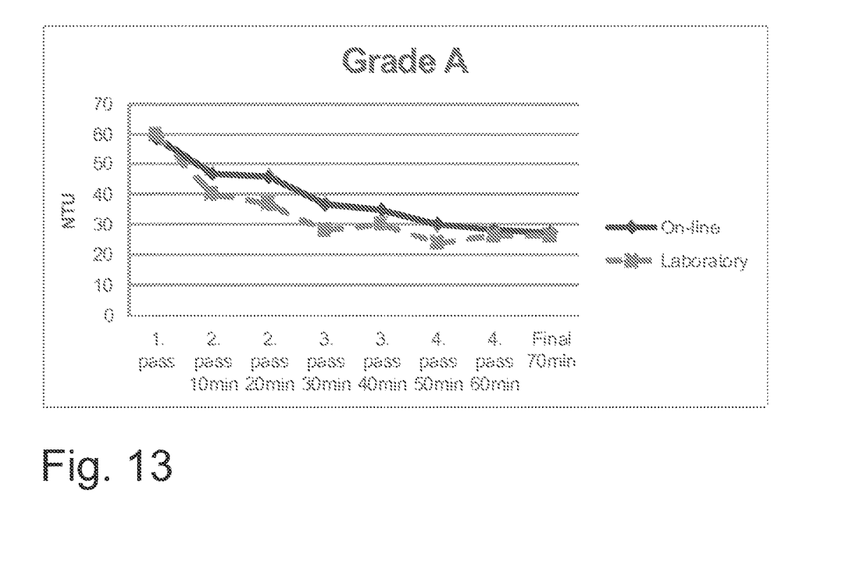
FIG. 13 shows results from a test wherein in-line measurements are compared to laboratory measurements at different time points and number of passes using Grade A pulp
Figure 14:
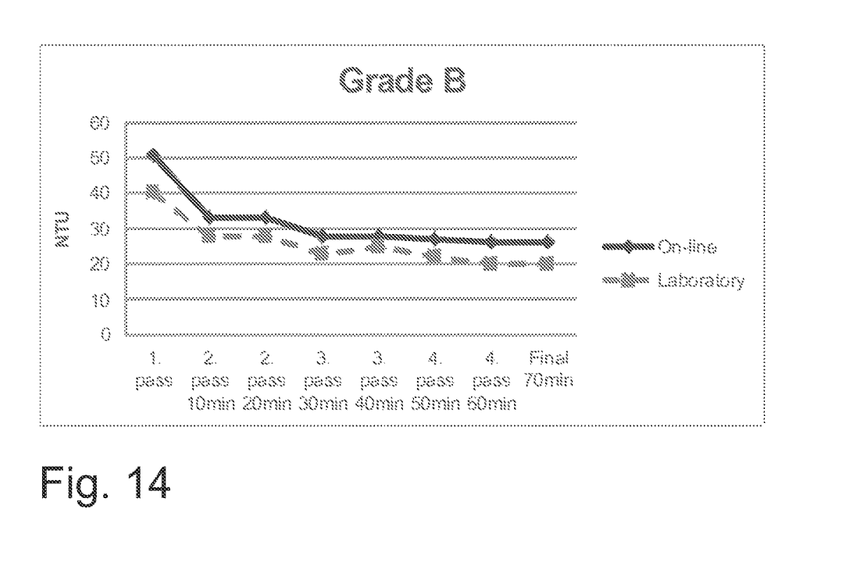
FIG. 14 shows results from a test wherein in-line measurements are compared to laboratory measurements at different time points and number of passes using Grade B pulp
Figure 15:
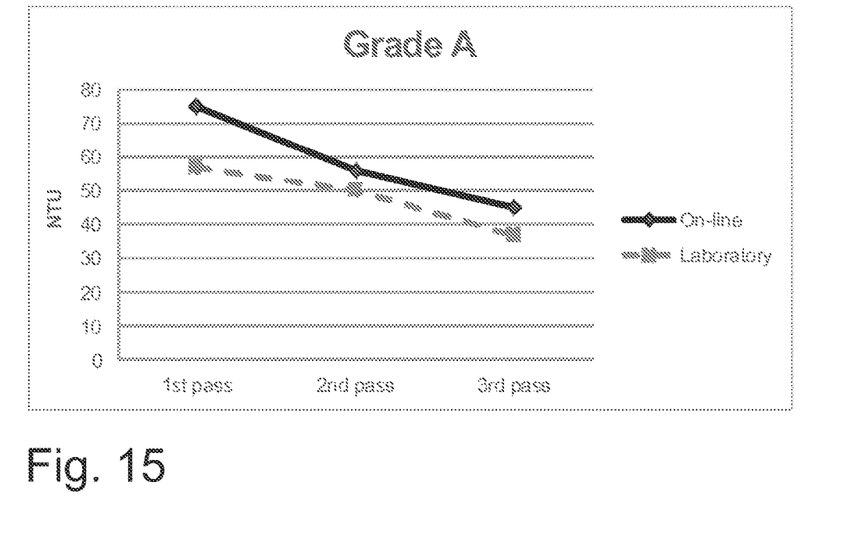
FIG. 15 shows results from a test wherein in-line measurements are compared to laboratory measurements at different number of passes using Grade A pulp

In the method the correlation between the measured turbidity and said quality of the produced nanofibrillar cellulose is used to determine the quality of the produced nanofibrillar cellulose. In practice, lowered turbidity indicates increased quality of the nanofibrillar cellulose. The correlation can also be defined as a correlation between the measured transparency and said quality of the produced nanofibrillar cellulose, i.e. the transparency of the dispersion or a change therein is measured. The measurement may be calibrated by using conventional laboratory analyses. In one example the turbidity is measured at a laboratory as NTUs and compared to the reading from an in-line meter. FIGS. 13, 14 and 15 show examples wherein in-line measurements are compared to laboratory measurements to demonstrate the correlation.

Figure 4:
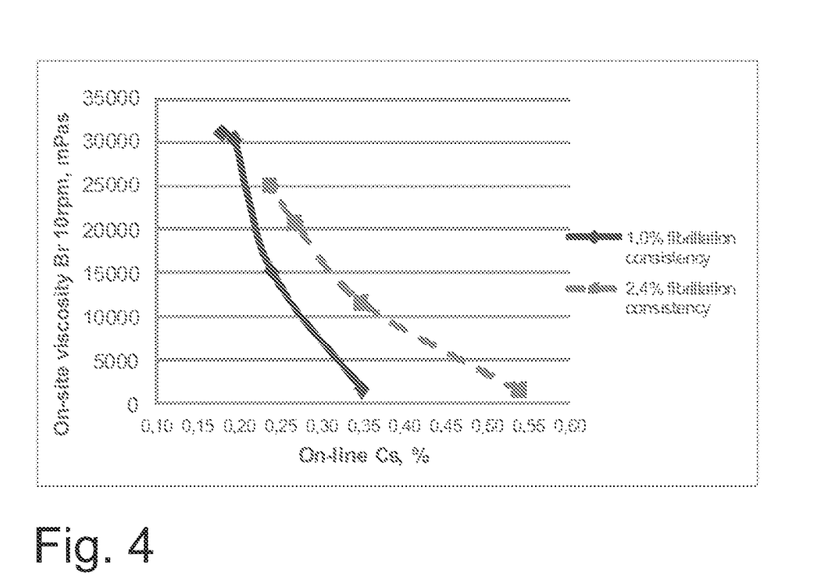
FIG. 4 shows results from a test wherein on-site viscosity is compared to in-line measurements at consistencies of 1.0% and 2.4%

In one example the correlation is determined between a viscosity determined at a laboratory and the in-line turbidity. FIG. 4 shows an example of the correlation of on-site viscosity with in-line measurements. The viscosity rises to a desired level while the turbidity lowers. However, this correlation may be slightly unlinear, as in the case of highly developed nanocellulose the viscosity is still increasing while the turbidity value is already setting.

In one embodiment the quality of the nanofibrillar cellulose comprises a fibrillation degree of said nanofibrillar cellulose. In one embodiment the quality of the nanofibrillar cellulose comprises a viscosity degree of said nanofibrillar cellulose.

In one embodiment the flow rate of the dispersion containing nanofibrillar cellulose is in the range of 0.01 m/s-5 m/s, such as in the range of 0.1-3 m/s. The flow rate has generally more effect to the disintegrating process than in the measurement itself. However, the flow rate should not be so high that there would be turbulences in the flow. In many systems the upper limit may be about 20 l/s, so an useful flow rate may be in the range of 1-14 l/s, for example 1-10 l/s, or 1-8 l/s. This however depends on the size of the equipment used, such as the diameter of the tubes and the like. Very high flow rates may be obtained if more than one disintegrating devices are connected in parallel.

The method is especially suitable for modified or chemical pulp or cellulose, as it is less coarse than native or untreated pulp and has a smaller diameter and therefore higher transparency. However, also native pulps may be monitored with the method. In one embodiment the pulp is native or non-modified pulp or cellulose. In one embodiment the pulp is modified pulp or cellulose, for example chemically modified pulp or cellulose, such as anionic pulp or cellulose or cationic pulp or cellulose, or enzymatically modified pulp or cellulose. In one example the pulp is anionic pulp. In one example the pulp is cationic pulp. In one example the pulp is oxidized pulp. In one example the pulp is TEMPO-oxidized pulp. If the pulp is oxidized, it usually has a higher transparency. For example anionic pulp will disintegrate into nanosize more easily. Said native or chemically treated pulps or celluloses discussed herein may refer to the pulp as the starting material or to the nanofibrillar cellulose or cellulose nanofibrils as the end product, or to any intermediate product obtained in the process.

In the oxidation of cellulose, the primary hydroxyl groups of cellulose are oxidized catalytically by a heterocyclic nitroxyl compound, for example 2,2,6,6-tetramethylpiperidinyl-1-oxy free radical, generally called "TEMPO". These hydroxyl groups are oxidized to aldehydes and carboxyl groups. Thus, part of the hydroxyl groups that are subjected to oxidation may exist as aldehyde groups in the oxidized cellulose, or the oxidation to carboxyl groups may be complete.

Figure 1:
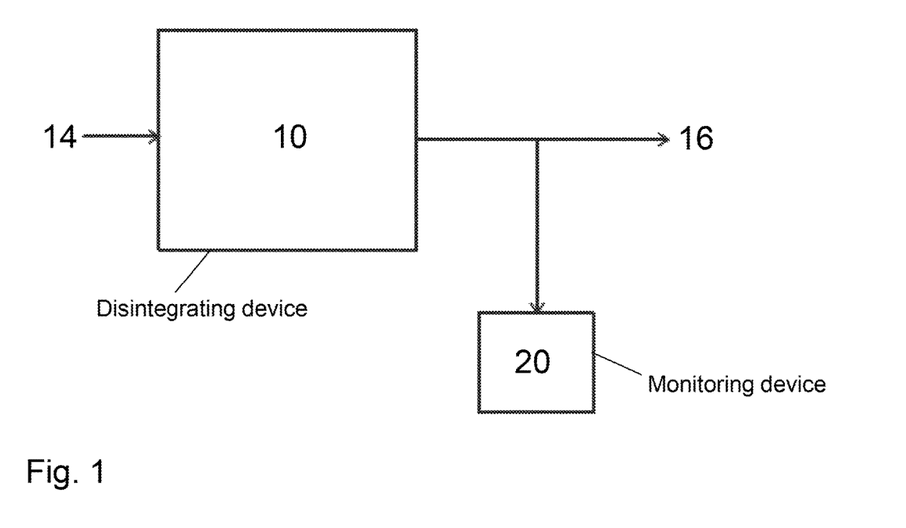
FIG. 1 shows an exemplary setup of a disintegrating device and a monitoring device for measuring the flow from the disintegration device

One embodiment provides a device for monitoring the quality of nanofibrillar cellulose produced in a process comprising disintegrating fibers of cellulose pulp, generally using one or more pulp disintegrating devices. In one example as illustrated in FIG. 1, the device 20 is connected to an output from a pulp disintegrating device 10 for monitoring a dispersion 16 containing said produced nanofibrillar cellulose obtained from said disintegrating device 10. The incoming flow to the disintegrated device 10 is marked as 14. More generally, the device is arranged to monitor a dispersion containing said produced nanofibrillar cellulose obtained from said disintegrating device. Therefore the device for monitoring the quality of nanofibrillar cellulose may be connected directly to the disintegrating device, or for example to a separate bypass line or outlet tube coming from said disintegrating device, or the produced nanofibrillar cellulose may be monitored from a flow coming from the disintegrating process, to carry out the real-time monitoring.

As the measurement is made continuously in a flow of the produced dispersion, a continuous signal is obtained producing continuous results or a continuous series of values representing the results.

The device for monitoring the quality of nanofibrillar cellulose comprises
  means for measuring optically the turbidity of said dispersion in real-time, and
  means for defining or determining the quality of said produced nanofibrillar cellulose using a correlation between the measured turbidity and said quality of the produced nanofibrillar cellulose. When using this correlation a lowered turbidity indicates increased quality of the nanofibrillar cellulose.

In one example the means for measuring optically the turbidity of said dispersion comprise an optical sensor which may be positioned to a suitable location in the flow, and the means for determining the quality of said produced nanofibrillar cellulose comprise a processing unit, which is connected to the optical sensor, for example with wires or wirelessly using any suitable wireless technology. In another example the sensor and the processing unit are in the same unit.

The means for measuring the turbidity of said dispersion comprise an optical measuring device, which may be arranged to measure light scattering, absorption, or a change in the polarization of scattered light, as described above.

In one embodiment the means for measuring optically the turbidity of said dispersion in real-time comprise a turbidimeter. In one embodiment the means for measuring optically the turbidity of said dispersion in real-time comprise a nephelometer. In one embodiment the means for measuring optically the turbidity of said dispersion in real-time comprise an absorption turbidimeter or a transmission turbidimeter.

The means for determining the quality of said produced nanofibrillar cellulose using a correlation between the measured turbidity and said quality of the produced nanofibrillar cellulose may comprise a processor or processing unit configured to determine the quality of the produced nanofibrillar cellulose using said correlation, generally using a specific software. The processor or processing unit may be a part of a controller unit or a computer connected to the optical measuring device. The processor may be operably connected to an interface, such as a display, printer, or an interface connected to any further device, such as a computer, a controller or a control unit arranged to control the one or more disintegrating devices, for example to adjust the operation speed of the disintegrating device. The controller or the control unit may also be arranged to adjust the flow speed of the dispersion to a disintegrating device. One example provides a software product comprising an executable program code configured to determine the quality of said produced nanofibrillar cellulose using the correlation between the measured turbidity and said quality of the produced nanofibrillar cellulose, wherein lowered turbidity indicates increased quality of the nanofibrillar cellulose. A program code for controlling the disintegrating device as a feedback may also be included. The program code is computer-executable and may be stored therein operative to perform said determination of the quality when executed on a computer. One example further provides a computer system having said executable program code.

The measured information obtained substantially in real-time is input to the means for determining the quality of said produced nanofibrillar cellulose, said means calculating a value representing the quality of the product at a certain time point. Further, this value is used in real-time for outputting the result of the measurement, or for controlling the disintegrating device(s) by adjusting the running parameters as a feedback for the determined quality value(s). For example, the speed of a disintegrating device may be adjusted in response to a quality value which does not fulfill predefined criteria. In another example the flow rate of the dispersion is adjusted as a response to the measurements.

One embodiment provides a device setup comprising said device connected to at least one pulp disintegrating device. For example, the measuring device may be connected to a pipeline after a discharge pump from the disintegrating device. The length of the pipeline may be for example in the range of 0.5-2 m, or longer.

In one embodiment the pulp disintegrating or fibrillating device is selected from a rotor-rotor dispergator, a disperser, a homogenizer, a refiner, a grinder, a colloider, a friction grinder, a pin mill, an ultrasound sonicator, and a fluidizer.

In one embodiment the disintegrating is carried out by using a disperser having at least one rotor, blade, or similar moving mechanical member, such as a rotor-rotor dispergator, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after each other at a high peripheral speed from opposite directions; in other words, it receives several successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor dispergator the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor dispergator is an Atrex device.

Another example of a device suitable for disintegrating is a pin mill, such as a multi-peripheral pin mill. One example of such device, as described in U.S. Pat. No. 6,202,946 B1, includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one embodiment the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion cause shearing and impact forces on the dispersion, resulting in the removal of fibrils from the fiber material. The fiber fragments are disintegrated into fibrils in the fibrillating step.

Figure 2:
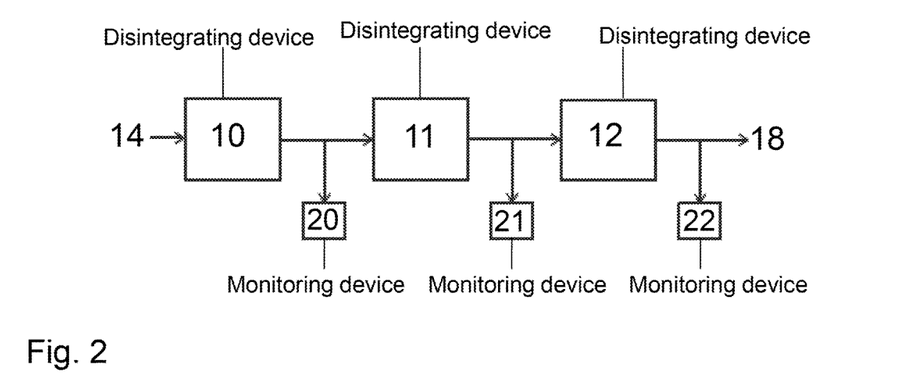
FIG. 2 shows an exemplary setup of four disintegrating devices wherein the turbidity may be measured separately after each device

In one embodiment the setup comprises at least two disintegrating devices, for example two, three or four disintegrating devices, which may be of the same type or of different types. Generally, the measurement is done at least from the flow obtained from the last device, but also the output from any of the previous devices may be monitored as well. FIG. 2 illustrates an example wherein three disintegrating devices 10, 11, 12 are connected in series. The cellulose-containing flow-in 14 enters the first device 10 and the finished fibrillar cellulose 18 which has undergone these three passes enters from the last device 12. From each disintegrating device 10, 1, 12 there is an output for three monitoring devices 20, 21, 22, each of which monitor an outlet from each disintegrating device 10, 11, 12.

In one embodiment the setup comprises at least two devices for monitoring the quality of nanofibrillar cellulose, each connected to a different one of said at least two disintegrated devices. In one example there is equal number of the monitoring devices and the disintegrating devices, such as two, three or four of both devices.

In one example the pulp is oxidized and applied through three or four refining devices, for example at least one rotor-rotor dispergator, and the product may be measured after each device. In one example the last refiner 12 is a finishing refiner and the settings thereof are adjusted according to the measurements from the previous refiner.

In one embodiment the device setup comprises one or more controlling means arranged to control said at least one disintegrating device as a feedback for the monitored quality of the nanofibrillar cellulose obtained from said at least one disintegrating device. The feedback control may be used to enhance the quality of the product, or to optimize the production rate or the function of one or more of the disintegrating devices. The controlling means may be arranged to control said at least one disintegrating device by changing the speed of the disintegrating device, for example a refiner, or by changing the flow rate of the pulp dispersion into the disintegrating device. For example if the flow rate seems to be too high resulting in incomplete fibrillation of the pulp or if interfering air bubbles begin to form in the dispersion, the flow rate can be adjusted, for example lowered, as a response to the measurements to obtain an optimal fibrillation and/or measurement result. In one example the system contains 3 or 4 disintegrating devices, and the pulp is fed to the first ones with full speed. The speed of the last disintegrating device may be controlled and if the fibrillation result deviates from the predefined desired values, the operating speed of the last disintegrating device is changed, for example lowered. In one example the fibrillation is carried out by recycling the pulp through the same disintegrating device via a container 3 or 4 times. If the fibrillation result is acceptable after the third round, there is no need for fourth round.

The controlling means may comprise a controller configured to carry out one or more of the actions described above to control at least one disintegrating device, pump device and/or other related device(s). The controller may comprise a processor or a processing unit. Such a processor or processing unit may be a part of a controller unit or a computer connected to the device. The controlling means are usually operatively connected to the device, for example they are arranged to operate one or more actuators in a device or to change the settings of a device for adjusting and controlling the device.

Examples

In the nephelometric laboratory method a nanofibrillar cellulose sample is diluted in water, to a concentration below the gel point of said nanofibrillar cellulose, to a measuring concentration of 0.1 wt-%. HACH P2100 Turbidometer with a 50 ml measuring vessel is used for turbidity measurements. The dry matter of the nanofibrillar cellulose sample is determined and 0.5 g of the sample, calculated as dry matter, is loaded into a measuring vessel, which is filled with tap water to 500 g and vigorously mixed by shaking for about 30 s. Without delay the aqueous mixture is divided into 5 measuring vessels, which are inserted into the turbidometer. Three measurements on each vessel are carried out. A mean value and standard deviation are calculated from the obtained results, and the final result is provided as NTU units (nephelometric turbidity units).

Objective of the tests was to find out if it was possible to use in-line turbidity measurements provided by Satron VO optical transmitter in fibrillation. Main challenges were the effect of relatively high consistency (2.4%) and air bubbles in the gel flow.

Equipment

Satron VO Optical Consistency Transmitter was used as an optical measuring device at 880 nm. A rotor-rotor dispergator device was used as a disintegrating device at a pilot plant. Instrumentation was assembled through a valve which was installed in vertical 1 meter long 100 mm diameter pipeline after the discharge pump of the dispergator. Unit included both the instrument itself and a small display screen.

Pulp

Cellulose birch pulp was anionically modified by "TEMPO" oxidation. Two modification levels we used: 0.95 mmol COOH/g pulp (Grade A) and 0.78 mmol COOH/g pulp (Grade B).

Fibrillation Example

Anionic pulp was dispersed into water to form 2.5% (w/w) dispersion. The flow (f) was 3 l/s, and the flow speed (v) at the point where the Satron device was installed was 0.4 m/s. The dispersion was run 4 times through a disperser (Atrex), through a series of counter rotating rotors. The disperser used had a diameter of 850 mm and rotation speed used was 1800 rpm. As a result, a viscous nanofibrillar cellulose gel was formed.

Samples

Anionic cellulose pulp (Grade A) was fibrillated at three different consistencies.
  2.5% (4 passes)
  1.5% (only the 4th pass)
  1.0% (4 passes)

Anionic cellulose pulp (Grade B) was fibrillated as described above.

Results

The results from Satron (presented as Cs %) and on-site turbidity during fibrillation is presented in FIGS. 3-15. The on-site measurements were carried out at a laboratory. It should be noted that the on-site turbidity was measured always at 0.15% consistency after a dilution.

Figure 3:
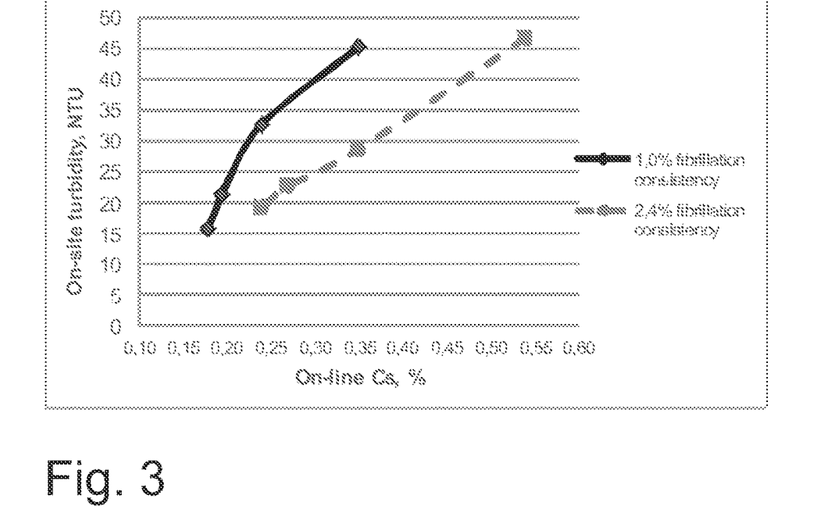
FIG. 3 shows results from a test wherein on-site (laboratory measurement) turbidity is compared to in-line measurements at consistencies of 1.0% and 2.4%

FIG. 3 shows results from a test wherein on-site (laboratory measurement) turbidity is compared to in-line measurements at consistencies of 1.0% and 2.4%. As can be seen, in-line turbidity correlates with laboratory measurement.

FIG. 4 shows results from a test wherein on-site viscosity is compared to in-line measurements at consistencies of 1.0% and 2.4%. When turbidity decreases the viscosity increases meaning that in-line measurement correlates to development of nanofibrillar cellulose quality.

Figure 5:
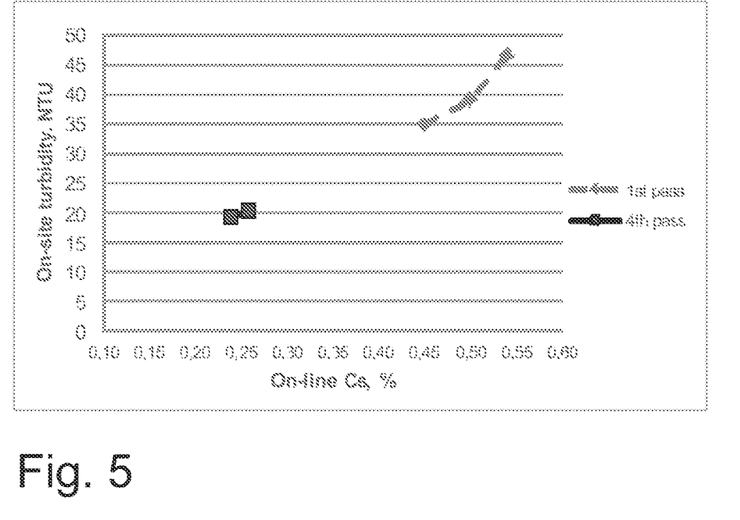
FIG. 5 shows results from a test wherein on-site turbidity is compared to in-line measurements after $1^{st}$ pass and $4^{th}$ pass
Figure 6:
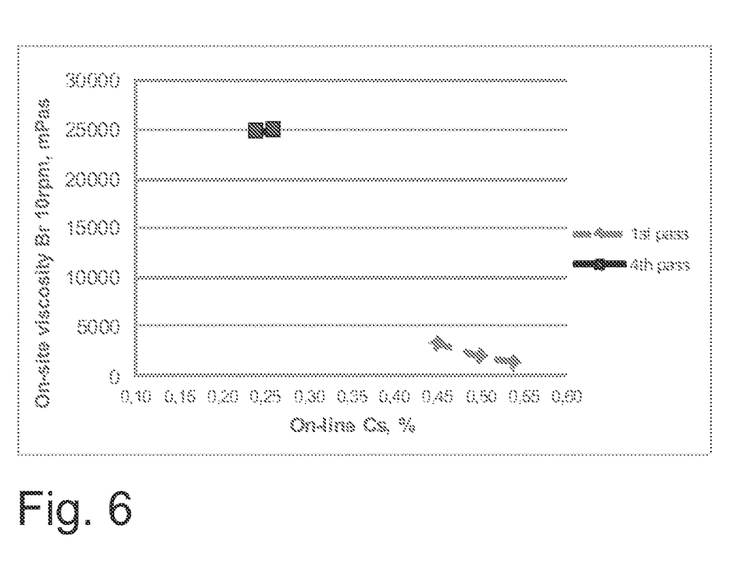
FIG. 6 shows results from a test wherein on-site viscosity is compared to in-line measurements after $1^{st}$ pass and $4^{th}$ pass

FIG. 5 shows results from a test wherein on-site turbidity is compared to in-line measurements after 1st pass and 4th pass. FIG. 6 shows results from a test wherein on-site viscosity is compared to in-line measurements after 1st pass and 4th pass. When turbidity decreased the viscosity increases meaning that in-line measurement correlates to development of nanofibrillar cellulose quality.

Figure 7:
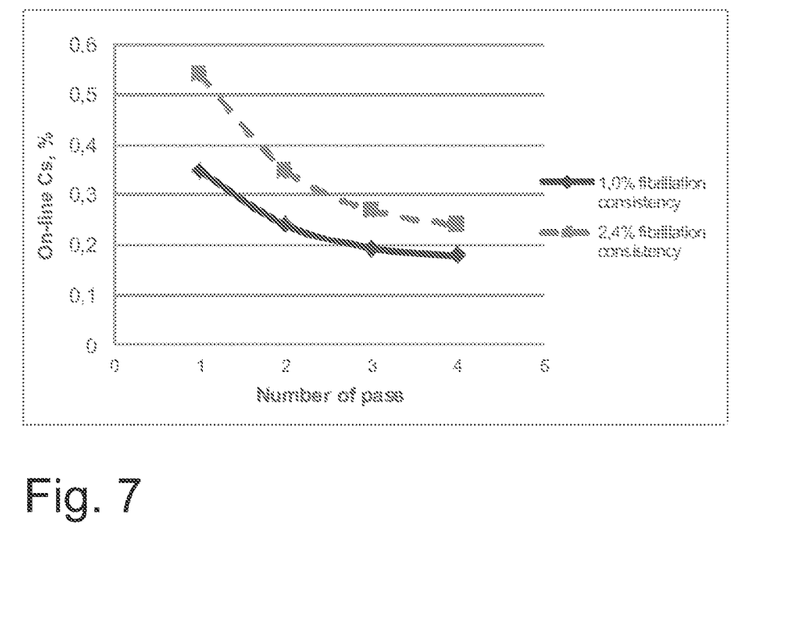
FIG. 7 shows results from a test wherein the in-line measurement is carried out after different number of passes at consistencies of 1.0% and 2.4%

FIG. 7 shows results from a test wherein the in-line measurement is carried out after different number of passes at consistencies of 1.0% and 2.4%. Improvement of the quality can be observed. These results indicate that the method is not concentration-sensitive and that it is accurate also when high concentrations are used.

Figure 8:
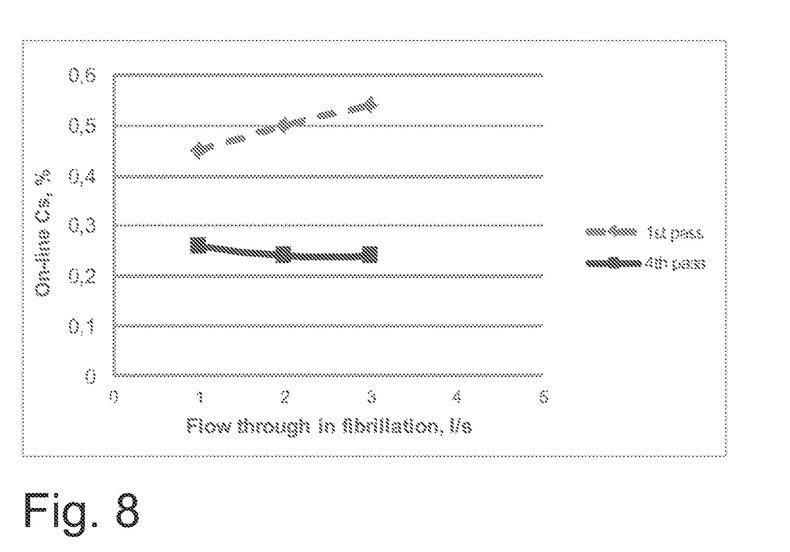
FIG. 8 shows results from a test wherein the in-line measurement is carried out at different flow rates after $1^{st}$ pass and $4^{th}$ pass

FIG. 8 shows results from a test wherein the in-line measurement is carried out at different flow rates after 1st pass and 4th pass. It can be seen that on-line measurement can detect the quality change which occurs when flow rate changes. For example, the quality of the nanofibrillar cellulose decreases when the flow rate increases (less energy is directed to the pulp).

Figure 9:
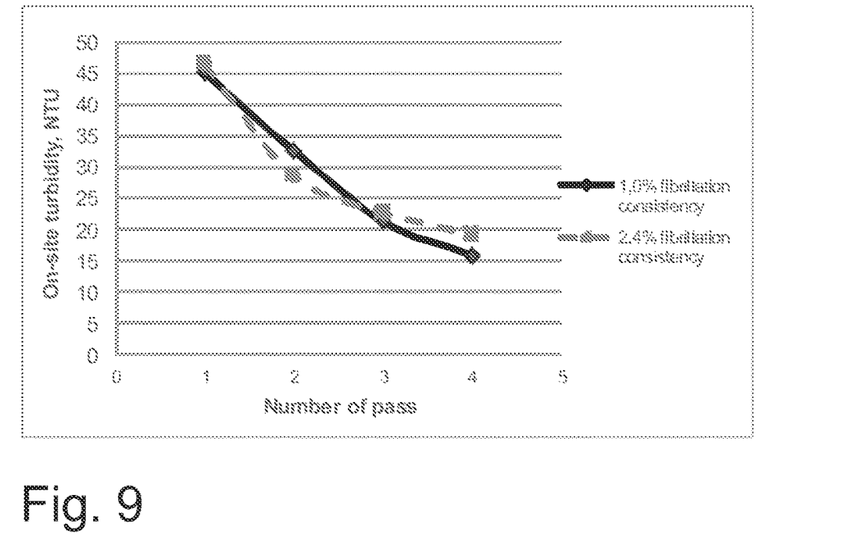
FIG. 9 shows results from a test wherein the on-site turbidity measurement is carried out after different number of passes at consistencies of 1.0% and 2.4%

FIG. 9 shows results from a test wherein the on-site turbidity measurement is carried out after different number of passes at consistencies of 1.0% and 2.4%. This is a laboratory reference to FIG. 7. It can be seen that the accuracy of the in-line measurement (FIG. 7) corresponds to the laborious laboratory measurement, especially when higher process concentrations are used.

Figure 10:
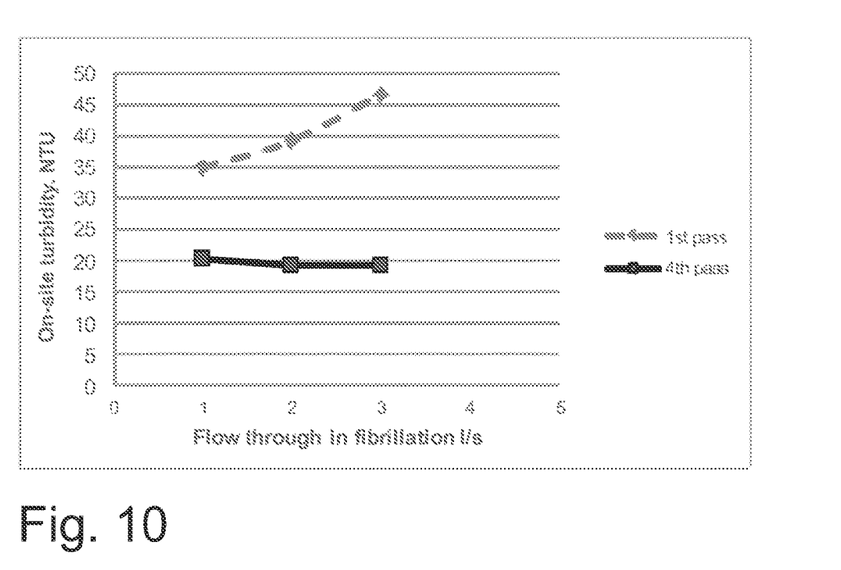
FIG. 10 shows results from a test wherein the on-site turbidity measurement is carried out at different flow rates after $1^{st}$ pass and $4^{th}$ pass

FIG. 10 shows results from a test wherein the on-site turbidity measurement is carried out at different flow rates after 1st pass and 4th pass. This is a laboratory reference to FIG. 8. It can be seen that the accuracy of the in-line measurement (FIG. 8) corresponds to the laborious laboratory measurement.

Figure 11:
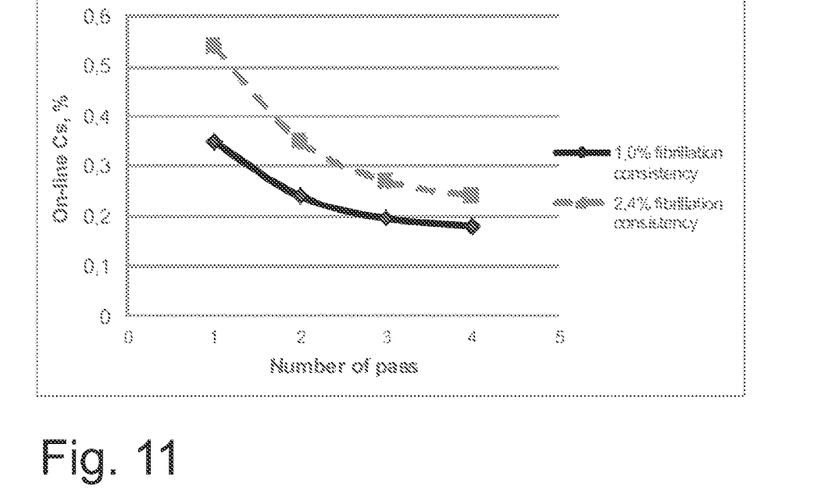
FIG. 11 shows results from a test wherein the in-line measurement is carried out after different number of passes at consistencies of 1.0% and 2.4%
Figure 12:
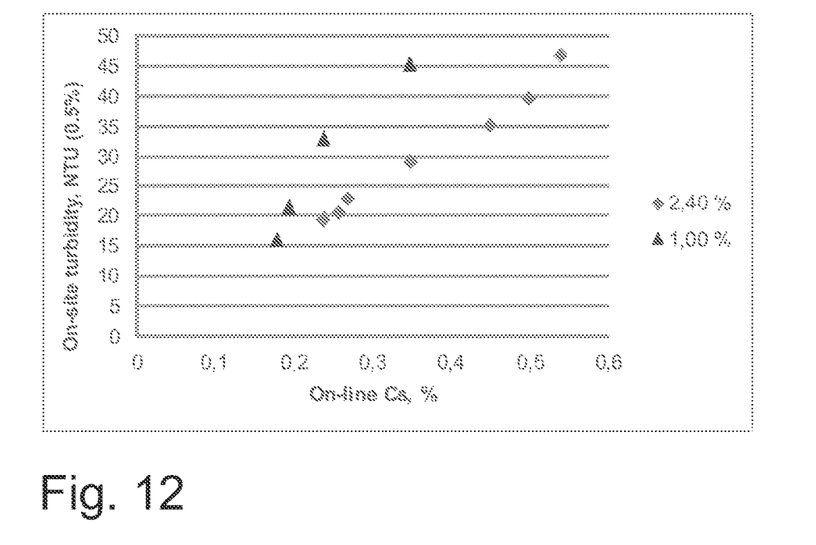
FIG. 12 shows results from a test wherein the in-line turbidity measurement is carried out after different number of passes at consistencies of 1.0% and 2.4%

FIG. 11 shows results from a test wherein the in-line measurement is carried out after different number of passes at consistencies of 1.0% and 2.4%. FIG. 12 shows results from a test wherein the in-line turbidity measurement is carried out after different number of passes at consistencies of 1.0% and 2.4%. This figure illustrates the correspondence of the in-line method to the laborious laboratory measurement.

FIG. 13 shows results from a test wherein in-line measurements are compared to laboratory measurements at different time points and number of passes using Grade A pulp. FIG. 14 shows results from a test wherein in-line measurements are compared to laboratory measurements at different time points and number of passes using Grade B pulp. FIG. 15 shows results from a test wherein in-line measurements are compared to laboratory measurements at different number of passes using Grade A pulp.

There is a very good correlation between on-site turbidity and Satron in-line measurement.

It was also seen that if discharge pump was running at too high speed and feeding air with gel, the overall level in display was higher and the variation extremely high. Therefore one must be very careful while adjusting the flow of discharge pump to avoid misunderstanding and incorrect values.

The invention claimed is:

1. A method for monitoring the quality of nanofibrillar cellulose produced in a process comprising disintegrating fibers of cellulose pulp, characterized in that the method comprises
  measuring in real-time optically the turbidity of a dispersion containing nanofibrillar cellulose obtained from said disintegrating process, and
  correlating the measured turbidity to the quality of the produced nanofibrillar cellulose to determine the quality of said produced nanofibrillar cellulose, wherein lowered turbidity indicates increased quality of the nanofibrillar cellulose.

2. The method of claim 1, wherein the turbidity measurement is carried out at a consistency of said dispersion in the range of 0.15-10%.

3. The method of claim 1, wherein the turbidity measurement is carried out at a consistency of said dispersion in the range of 0.5-8%.

4. The method of claim 1, wherein the turbidity measurement is carried out at a consistency of said dispersion in the range of 1-5%.

5. The method of claim 1, wherein the turbidity measurement is carried out at a consistency of said dispersion in the range of 1.5-4%.

6. The method of claim 1, wherein the quality of the nanofibrillar cellulose comprises a fibrillation degree of said nanofibrillar cellulose.

7. The method of claim 1, wherein the quality of the nanofibrillar cellulose comprises a viscosity degree of said nanofibrillar cellulose.

8. The method of claim 1, wherein the turbidity measurement is a light scattering measurement.

9. The method of claim 8, wherein a change in the polarization of the scattered light is measured.

10. The method of claim 8, wherein the polarization of the scattered light is measured.

11. The method of claim 1, wherein the turbidity measurement is an absorption measurement.

12. The method of claim 1, wherein the optical measurement is carried out at a wavelength in the range of 260-900 nm.

13. The method of claim 1, wherein the optical measurement is carried out at a wavelength in the range of 400-890 nm.

14. The method of claim 1, wherein the flow rate of the dispersion containing nanofibrillar cellulose is in the range of 0.01 m/s-5 m/s.

15. The method of claim 1, wherein the flow rate of the dispersion containing nanofibrillar cellulose is in the range of 0.1-3 m/s.

16. The method of claim 1, wherein the pulp is non-modified pulp.

17. The method of claim 1, wherein the pulp is modified pulp.

18. The method of claim 17 wherein the modified pulp is chemically modified pulp.

19. The method of claim 17 wherein the modified pulp is oxidized pulp.

20. The method of claim 19 wherein the oxidized pulp is TEMPO oxidized pulp.

21. The method of claim 17 wherein the modified pulp is anionic pulp.

22. The method of claim 17 wherein the modified pulp is cationic pulp.

23. The method of claim 17 wherein the modified pulp is enzymatically modified pulp.

24. The method of claim 1, wherein the disintegrating process is a continuous process.

25. The method of claim 1, wherein the real-time measurement is carried out as an in-line measurement from the process flow.

26. The method of claim 1, wherein the real-time measurement is carried out as an on-line measurement from a side flow.

27. A device for monitoring the quality of nanofibrillar cellulose produced in a disintegrating process comprising disintegrating fibers of cellulose pulp, characterized in that the disintegrating process comprises:
    measuring in real-time optically the turbidity of a dispersion containing nanofibrillar cellulose obtained from said disintegrating process, and
    correlating the measured turbidity to the quality of the produced nanofibrillar cellulose to determine the quality of said produced nanofibrillar cellulose, wherein lowered turbidity indicates increased quality of the nanofibrillar cellulose,
    the device being arranged to monitor a dispersion containing said produced nanofibrillar cellulose obtained from a disintegrating device, characterized in that the monitoring device comprises
    means for measuring optically the turbidity of said dispersion in real-time, and
    means for determining the quality of said produced nanofibrillar cellulose using a correlation between the measured turbidity and said quality of the produced nanofibrillar cellulose, wherein lowered turbidity indicates increased quality of the nanofibrillar cellulose.

28. The device of claim 27, wherein the means for measuring optically the turbidity of said dispersion in real-time comprise a turbidimeter.

29. The device of claim 28, wherein the means for measuring optically the turbidity of said dispersion in real-time comprise an absorption turbidimeter.

30. The device of claim 28, wherein the means for measuring optically the turbidity of said dispersion in real-time comprise a transmission turbidimeter.

31. The device of claim 27, wherein the means for measuring optically the turbidity of said dispersion in real-time comprise a nephelometer.

32. A device setup comprising the device of claim 27 connected to at least one pulp disintegrating device.

33. The device setup of claim 32, wherein the pulp disintegrating device is selected from a rotor-rotor dispergator, a disperser, a homogenizer, a refiner, a grinder, a colloider, a friction grinder, a pin mill, an ultrasound sonicator, and a fluidizer.

34. The device setup of claim 32, wherein the means for measuring optically the turbidity of said dispersion in real-time are connected directly to a disintegrating device.

35. The device setup of claim 32, wherein the means for measuring optically the turbidity of said dispersion in real-time are connected to a separate bypass line or outlet tube coming from a disintegrating device.

36. The device setup of claim 32, wherein the setup comprises at least two disintegrating devices.

37. The device setup of claim 36, wherein the setup comprises at least two devices for monitoring the quality of nanofibrillar cellulose each connected to a different one of said at least two disintegrated devices.

38. The device setup of claim 32, comprising controlling means arranged to control said at least one disintegrating device as a feedback for the monitored quality of the nanofibrillar cellulose obtained from said at least one disintegrating device.

39. The device setup of claim 38, wherein the controlling means are arranged to control said at least one disintegrating device by changing the speed of the disintegrating device.

40. The device setup of claim 38, wherein the controlling means are arranged to control said at least one disintegrating device by changing the flow rate of the pulp dispersion into the disintegrating device.

* * * * *